(12) United States Patent
Guyer et al.

(10) Patent No.: US 8,425,610 B2
(45) Date of Patent: Apr. 23, 2013

(54) INTERBODY SPACER

(75) Inventors: Jeffrey Guyer, San Diego, CA (US); Robert Lynn, Dove Canyon, CA (US)

(73) Assignee: Alphatec Spine, Inc., Carlsbad, CA (US)

(*) Notice: Subject to any disclaimer, the term of this patent is extended or adjusted under 35 U.S.C. 154(b) by 563 days.

(21) Appl. No.: 12/560,244

(22) Filed: Sep. 15, 2009

(65) Prior Publication Data
US 2010/0070039 A1  Mar. 18, 2010

Related U.S. Application Data

(60) Provisional application No. 61/192,210, filed on Sep. 16, 2008.

(51) Int. Cl.
*A61F 2/44* (2006.01)
(52) U.S. Cl.
USPC .......................................... 623/17.16

(58) Field of Classification Search ..... 623/17.11–17.16
See application file for complete search history.

(56) References Cited

U.S. PATENT DOCUMENTS

| | | |
|---|---|---|
| 2001/0049560 A1 | 12/2001 | Paul et al. |
| 2004/0059337 A1 | 3/2004 | Hanson et al. |
| 2005/0027360 A1* | 2/2005 | Webb et al. ............ 623/17.11 |
| 2008/0154377 A1 | 6/2008 | Voellmicke |

* cited by examiner

*Primary Examiner* — Sameh Boles
(74) *Attorney, Agent, or Firm* — Michael J. Loi

(57) ABSTRACT

An interbody spacer is provided. The spacer includes a housing having a top portion, a bottom portion, and a plurality of side portions disposed between the top portion and the bottom portion, a midline portion configured to be disposed across at least one of the top portion and the bottom portion of the housing, an opening disposed between the top portion and the bottom portion, and a grooved channel disposed in at least one of the plurality of side portions. The top and bottom portions are configured to include a plurality of projections configured to protrude away from the top and bottom portions.

17 Claims, 3 Drawing Sheets

INTERBODY SPACER

CROSS-REFERENCE TO RELATED APPLICATIONS

The present application claims priority to U.S. Provisional Patent Application No. 61/192,210, filed Sep. 16, 2008, entitled "Interbody Spacer". The present invention relates to U.S. patent application Ser. No. 11/903,895 to Murillo et al., filed Sep. 24, 2007, entitled "Spinal spacer", and claiming priority to U.S. Provisional Patent Application No. 60/846,568, filed Sep. 22, 2006. The present application also relates to U.S. patent application Ser. No. 12/069,721 to Garcia-Bengochea et al., filed Feb. 11, 2008, entitled "Curvilinear Spinal Access Method And Device", and claiming priority to U.S. Provisional Patent Application No. 60/900,554, filed Feb. 9, 2007. The present application also relates to U.S. patent application Ser. No. 12/460,795 to Jeffrey Guyer et al., filed Jul. 23, 2009, and entitled "Curvilinear Spinal Access Method and Device". The disclosures of the above-referenced patent applications are incorporated herein by reference in their entireties.

BACKGROUND OF THE INVENTION

1. Field of the Invention

The present invention is directed to systems, methods, and devices applicable to spinal surgery. More specifically, the present invention is directed to an interbody spacer for use by medical personnel (i.e., doctor) in spinal and other surgical procedures. Some embodiments of the present invention relate to an interbody spacer for insertion into a disk space defined between two adjacent vertebrae, in order to restore an appropriate height between the vertebrae and to allow bone fusion to take place between said adjacent vertebrae.

2. Background of the Invention

Vertebrae are the individual irregular bones that make up the spinal column (aka ischis)—a flexuous and flexible column. There are normally thirty-three vertebrae in humans, including the five that are fused to form the sacrum (the others are separated by intervertebral discs) and the four coccygeal bones which form the tailbone. The upper three regions comprise the remaining 24, and are grouped under the names cervical (7 vertebrae), thoracic (12 vertebrae) and lumbar (5 vertebrae), according to the regions they occupy. This number is sometimes increased by an additional vertebra in one region, or it may be diminished in one region, the deficiency often being supplied by an additional vertebra in another. The number of cervical vertebrae is, however, very rarely increased or diminished.

A typical vertebra consists of two essential parts: an anterior (front) segment, which is the vertebral body; and a posterior part—the vertebral (neural) arch—which encloses the vertebral foramen. The vertebral arch is formed by a pair of pedicles and a pair of laminae, and supports seven processes, four articular, two transverse, and one spinous, the latter also being known as the neural spine.

When the vertebrae are articulated with each other, the bodies form a strong pillar for the support of the head and trunk, and the vertebral foramina constitute a canal for the protection of the medulla spinalis (spinal cord), while between every pair of vertebrae are two apertures, the intervertebral foramina, one on either side, for the transmission of the spinal nerves and vessels.

Conventional interbody spacer assemblies are used in spinal fusion procedures to repair damaged or incorrectly articulating vertebrae. Conventional interbody spacer assemblies come in different cross sections. Some spacer assemblies may be hollow and may include openings in the side(s) thereof to provide access for bone matter growth.

Historically one of the failure modes of interbody spacers, designed to support and stabilize the anterior column of the spine, is one of migration. This has been previously addressed by incorporating features on the upper and lower surfaces of implants to resist migration. Some implant designs have integrated features that prevent the implant from migrating once installed but restrict the ease of implant insertion such as spikes and protrusions, creating a paradoxical relationship where implant manufacturers must choose between either making the implant easier to insert or making the implant less likely to migrate. Wedge features have been previously utilized to resist migration however have been limited in their application by preferentially resisting migration in limited directions, such as wedge designs that are only symmetric across the saggital plane.

There exists a need for further improvements in the field of interbody spacer assemblies of the present type.

SUMMARY OF THE INVENTION

The current invention solves these problems by using balanced features that uniformly restrict movement, including movement in at least one or all radial directions, yet allow easy insertion, including four directional wedge patterns or radial pattern. Additionally, the integration of a bone graft scoop acts to stabilize the implant while boney growth develops in the central columns by preliminarily forming woven bone between the implant scoop and annular wall. Further, in some embodiments, the present invention includes a midline trench that can be used to prevent migration by utilizing a "reverse keel" from the vertebral body to hold and guide the implant in place.

Present invention is a new lumbar interbody spacer design highlighting the following innovative features: (1) a quad directional wedge design which prevents migration in the anterior-posterior and lateral directions; (2) One or more graft scoops located at the leading edge and/or the tailing edge which allow a surgeon to pre and post pack an implant with graft material and DBM to aide in a more distributed fusion pattern; (3) midline trench cutout which can be used to guide the implant along rails located in a delivery device or a "reverse keel" cut into a vertebral body while also providing additional support to prevent migration.

In some embodiments, the present invention relates to an interbody spacer. The spacer includes a housing having a top portion, a bottom portion, and a plurality of side portions disposed between the top portion and the bottom portion, a midline portion configured to be disposed across at least one of the top portion and the bottom portion of the housing, an opening disposed between the top portion and the bottom portion, and a grooved channel disposed in at least one of the plurality of side portions. The top and bottom portions are configured to include a plurality of projections configured to protrude away from the top and bottom portions.

In some embodiments, the present invention relates to an interbody spacer assembly. The assembly includes an interbody spacer. The spacer includes a housing having a top portion, a bottom portion, two sides, a front portion, and a back portion, wherein the front and back portions are configured to be disposed between the two sides and wherein the front and back portions and the sides are configured to be disposed between the top and bottom portions. The front and back portions are configured to include have at least one curved portion. The spacer includes at least one side of the two sides includes at least one grooved channel. The housing further includes a midline portion disposed substantially across the housing. Two sides, the front and back portions, and the midline portion are configured to enclose at least one opening. The top and bottom portions are configured to include a plurality of protrusions configured to protrude away from the top and bottom portions.

Further features and advantages of the invention, as well as structure and operation of various embodiments of the invention, are disclosed in detail below with references to the accompanying drawings.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

Figure 1:
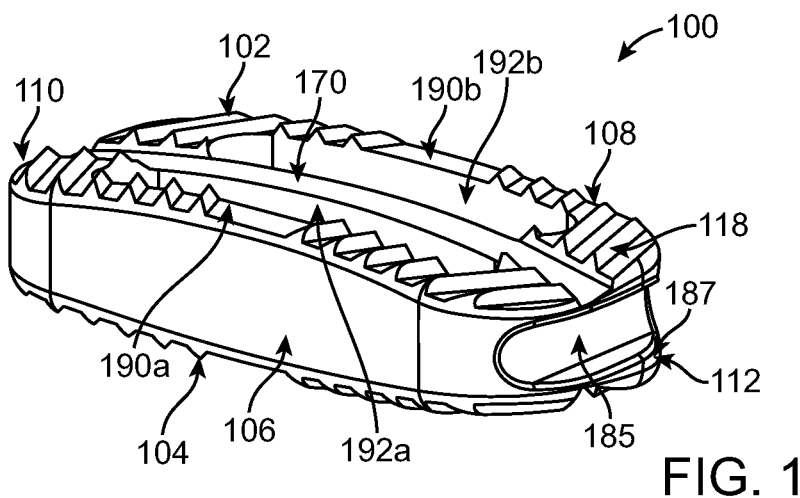
FIG. 1 is perspective view of an exemplary interbody spacer, according to embodiments of the present invention.

FIGS. 1-3b illustrate an interbody spacer 100 having a housing that includes a top portion 102, a bottom portion 104, a front side 106, a back side 108, a left side 110, and a right side 112. The front side 106, the back side 108, the left side 110 and the right side 112 may have a varying height, length, thickness, and/or curvature radius, as illustrated in FIGS. 1-3b. As further illustrated in FIGS. 1-3b, the sides 106, 108, 110, and 112 are configured to include at least one curved portion that can be configured to have a variable degree curvature radius.

Figure 2:
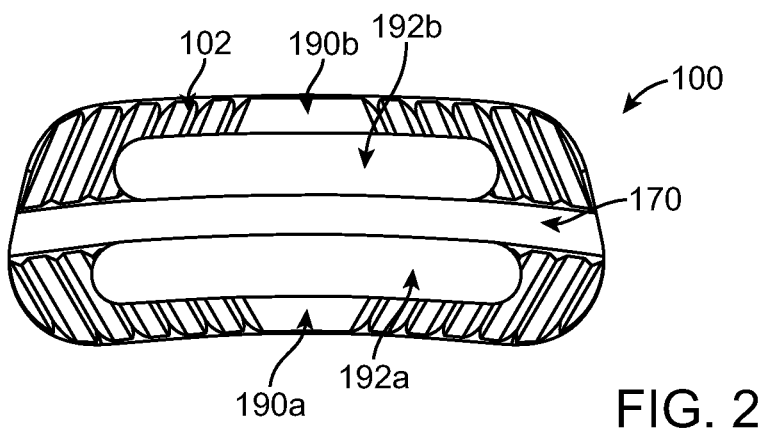
FIG. 2 is a top view of the exemplary interbody spacer shown in FIG. 1.

As shown in FIG. 1, the interbody spacer includes a midline trench 170 that is configured to be disposed longitudinally across the top portion 102. As can be understood by one skilled in the art, the bottom portion 104 can also include a midline trench 172 (as shown in FIG. 3b). The midline trenches 170, 172 are configured to assist a surgeon in guiding the interbody spacer 100 along rails located in a delivery device or a reverse keel cut into a vertebral body while also providing additional support to prevent migration of the interbody spacer 100, once the latter is installed into the vertebrae. The interbody spacer 100 further includes two openings 192 (a, b) that are disposed on each side of the midline trenches 170, 172, as shown in FIGS. 1-2. The openings 192 can be configured to allow graft and Demineralized Bone Matrix ("DBM") packing. In some embodiments, the openings 192 are configured to partially protrude into the body of the interbody spacer 100, hence, without creating a through channel. A combination of the sides 106, 108, 110, 112, as well as the midline trenches 170, 172 forms a wall that encloses the openings 192.

The top portion 102 and the bottom portion 104 include a plurality of protrusions or teeth 118 (hereinafter, referred to as "teeth"). Teeth 118 can be configured to be spaced throughout the top portion 102 and the bottom portion 104. As can be understood by one skilled, the teeth 118 can be configured to have variable thickness, height, and width as well as angles of orientation with respect to surfaces of portions 102 and 104. The teeth 118 can be further configured to provide additional support after the interbody spacer 100 is implanted in the vertebrae of the patient. The teeth 118 can reduce movement of the interbody spacer 100 in the vertebrae and create additional friction between the vertebrae and the spacer 100. In some embodiments, more than one interbody spacer 100 can be implanted in the vertebrae of the patient. In such embodiments, multiple interbody spacers can be placed in a side-by-side configuration or any other suitable configuration, thereby creating additional support. The teeth 118 can be configured to have a shape of triangular protrusions extending away from the surfaces of the top and bottom portions of the interbody spacer 100. The triangular protrusions can be configured to be right-angled isosceles triangles. As can be understood by one skilled in the art, the triangular protrusions can be any size and shape triangles are not necessarily limited to the right-angled isosceles triangles. As can be understood by one skilled in the art, the teeth 118 can be configured to have any shape, size, and/or angular or any other orientation as well as can protrude any distance away from the surfaces of the interbody spacer and can have any distance between them. In some embodiments, the tooth patterns have a quad-directional configuration (i.e., teeth 118 are facing in four different directions).

Referring back to FIGS. 1-3a, in some embodiments, the teeth 118 can be configured to be evenly spaced on the top portion 102 and the bottom portion 104. In other embodiments, the teeth 118 can be configured to be spaced in a predetermined order, such as the one shown in FIGS. 1-3a.

As show in FIG. 1, the top surface 102 (and/or the bottom surface 104) can include a cut-out portions 190 (a, b) disposed between the teeth 118 substantially adjacent each of the side portions 106, 108. These cut-out portions 190 can be configured to provide additional support to the interbody spacer 100 when it is implanted into vertebrae and create additional friction, thereby preventing movement of the spacer 100. Further, the interbody spacer 100 is thus easier to implant because of at least the additional support and relief created by the cut-out portions 190.

FIG. 2 is a top view of the exemplary interbody spacer 100 shown in FIG. 1. As previously discussed, the top surface 102 also includes a plurality of teeth 118. The teeth 118 can be disposed through the top surface 102 in a similar fashion as their counterparts in the bottom surface 104 (not shown). The teeth disposition can be substantially symmetrical about a center axis of the spacer 100. As can be understood by one skilled in the art, such symmetrical disposition can be in the top surface 102 as well as in the bottom surface 104 of the interbody spacer 100. As shown in FIG. 2, the length of the teeth 118 can vary throughout the top portion 102. In some embodiments, the teeth 118 can have a greater length near the right and left sides of the spacer 100 and shorter length near the front and back sides of the spacer 100. Further, the spacer 100 further includes a wall that is disposed about openings 192. In some embodiments, the wall formed adjacent to the right and left sides of the interbody spacer 100 can be configured to have a smaller thickness than the thickness of the wall formed adjacent to the front and back portions of the spacer 100. In some embodiments, the thicknesses of the front portion, back portion, and left side can be configured to be substantially the same.

Figure 3A:
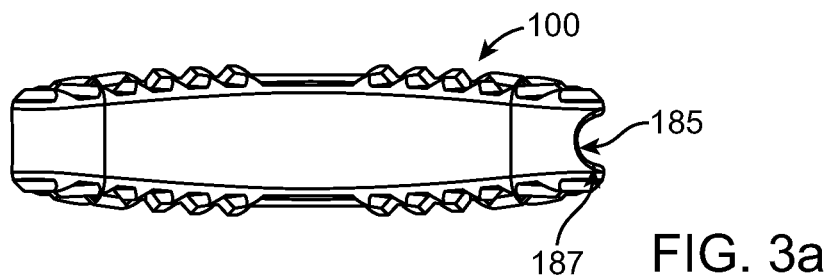
FIGS. 3a, 3b and 3c are side views of the exemplary interbody spacer shown in FIG. 1.
Figure 3B:
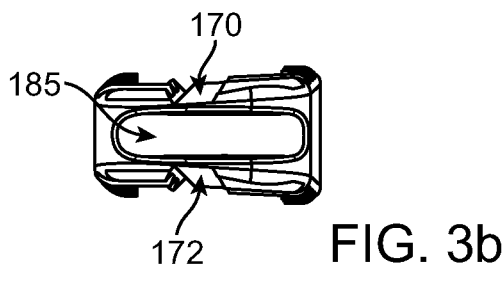

FIGS. 3a-b are side views of the exemplary interbody spacer 100 illustrated in FIG. 1. As illustrated in FIG. 3b, the left side 110 of the interbody spacer 100 can be configured to have a lesser thickness than the thickness of the right side 112 of the interbody spacer 100.

The sides 106 and 108 may have varying degrees convexity and concavity, as illustrated in FIG. 1. The various curvatures of the interbody spacer 100 can be configured to closely match the shape of the vertebrae discs of the patient. This way, the interbody spacer allows better movement and flexibility of the vertebrae with the spacer installed. As can be understood by one skilled in the art, the sides 108 and 110 may have varying heights. For example, the height of side 108 can be greater than the height of side 110. Further, in some embodiments, the height of sides 106, 108, 110, and 112 can vary throughout the device, as desired. For example, the height of at least a portion of the side 106 can be greater than the height of at least a portion of the side 108. The height can also vary within each side 106, 108, 110, and 112. This means that, for example, a portion of the left side 110 can have a lesser height than another portion of the left side 110. Such variation in heights throughout the sides of the interbody spacer 100 can be based on a particular design choice and further configured to accommodate various dimensions of the vertebrae of the patient. Also, the thickness of the walls can vary between the sides 106, 108, 110, and 112. The thickness can also vary within each side 106, 108, 110, and 112. This means that, for example, the thickness of at least a portion of the right side 112 can greater than the thickness of at least another portion of the right side 112.

Figure 3C:
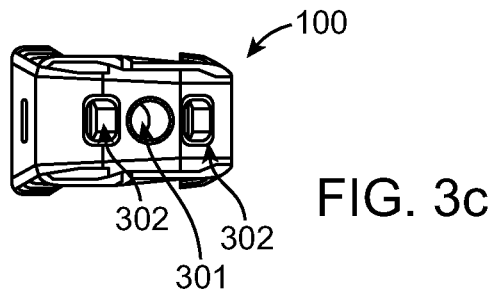

Referring to FIGS. 3a-c, the right side 112 can be configured to include a scoop portion 185. In some embodiments, the scoop portion 185 can be configured as a grooved channel formed in the wall of the right side 110 of the interbody spacer 100. The scoop portion can be configured to create an additional area for graft and DBM packing at a trailing/leading edge of the interbody spacer 100. As one skilled in the art would appreciate, the scoop portion 185 can be configured in any shape or size conducive to holding graft such as elliptical, circular, rectangular, and semi-circular. In some embodiments, the left side 110 or any other side of the spacer 100 can include such grooved channels for graft/DBM or any other purposes. The right side 112 also include a bulleted leading edge 187 disposed on the bottom portion 104 (as can be understood by one skilled in the art, the edge 187 can be disposed on any portion of the spacer 100) that is configured to self-distract into the disc space upon installation of the interbody spacer 100. The combination of the grooved channel(s) (i.e., scoop portion(s) 185) and the edge(s) 187 allows a surgeon to pre- and post-pack the spacer 100 with graft material and DBM in order to aide in a more distributed fusion pattern and stabilize the implant (i.e., the interbody spacer 100) with woven bone during fusion process. Either side can also feature one or more threaded circular apertures 301 which can be configured to be attachment points for instrumentation. The sides may also include one or more windows 302 which may also be attachment points for instrumentation.

Figure 4:
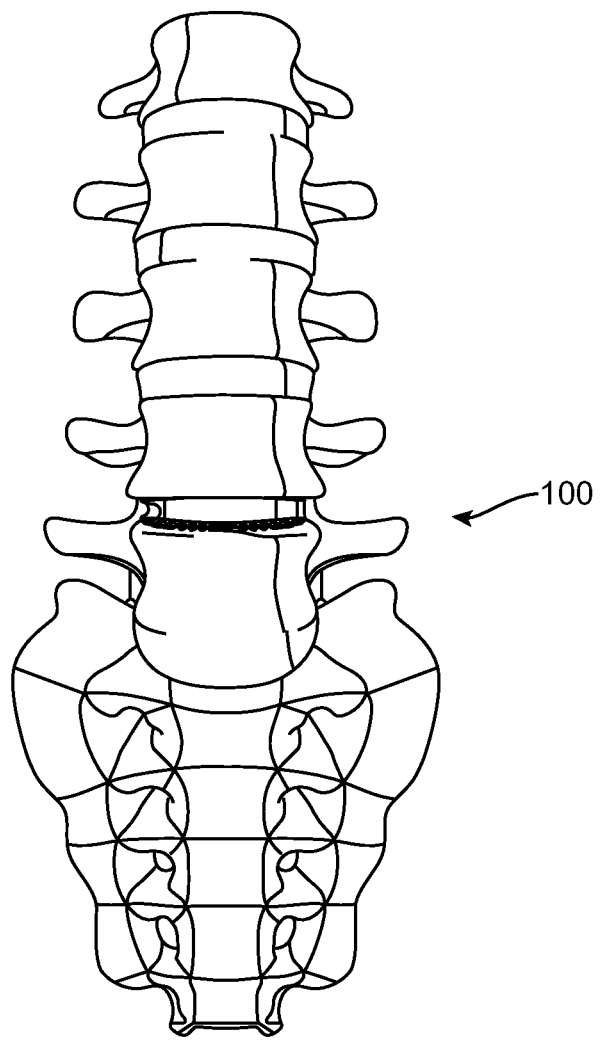
FIG. 4 illustrates an exemplary interbody spacer being installed into a vertebra, according to some embodiments of the present invention.
Figure 5:
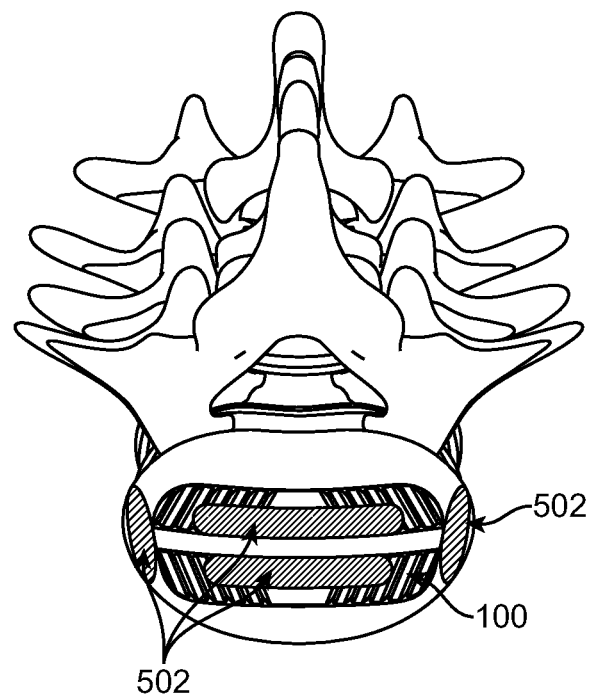
FIG. 5 is an enlarged view of the exemplary interbody spacer being installed into a vertebra, according to some embodiments of the present invention.

FIGS. 4 and 5 illustrate installation of the interbody spacer into patient's vertebrae. FIG. 4 illustrates an installed interbody spacer 100. FIG. 5 illustrates an enlarged portion of the FIG. 4 showing the installed interbody spacer 100 in greater detail. The shaded areas 502 illustrate projected fusion patterns of the bony matter.

Figure 6:
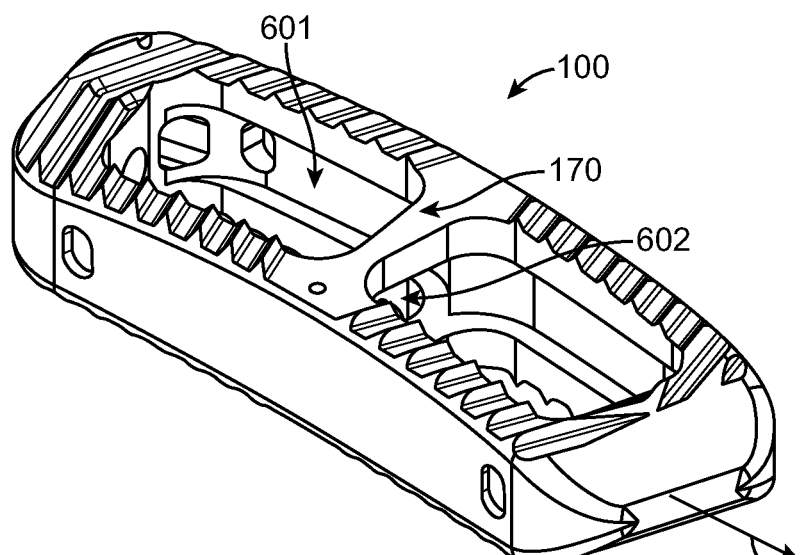
FIG. 6 is a perspective view of an exemplary interbody spacer, according to embodiments of the present invention.

FIG. 6 shows another embodiment of the interbody spacer. In this illustration, the spacer 100 features such as a sidewall trench 601 may be used as a shelf for the graft, among other uses. The midline trench opening 602 allows graft material to be more securely contained within the implant.

In some embodiments, the interbody spacer 100 can be manufactured from a biologically accepted inert material, such as PEEK (Polyetheretherketone). The spacer can be configured to be implanted between the vertebrae for treating degenerative or ruptured discs and/or for replacing damaged vertebral bodies. As stated above, the spacer can be configured to be used singularly or in combination with other interbody spacers 100 in an exemplary side-by-side or any other suitable configuration to fill differently sized evacuated spaces. Each spacer can be particularly shaped and sized for its particular application.

In some embodiments, the interbody spacer 100 can be sized larger than the vertebral body and/or configured to be implanted so that it rests on an apophyseal ring of a vertebrae (which is one of the strongest portions in a vertebral body). As can be understood by one skilled in the art, the interbody spacer 100 can be sized and shaped as well as implanted as desired in accordance with a particular medical necessity or other factors.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. An interbody spacer, comprising:
a housing having a top portion, a bottom portion, a front side, a back side, a left side, and a right side disposed between said top portion and said bottom portion;
a midline portion extending between and connecting said front side and back side configured to be disposed between said top portion and said bottom portion of said housing;
openings disposed on each side of said midline portion between said top portion and said bottom portion;
a sidewall trench disposed in at least one of said front side or back side within said openings configured to provide an additional area for graft packing during implantation of the interbody spacer between vertebrae; and
said top and bottom portions are configured to include a plurality of projections configured to protrude away from said top and bottom portions.

2. The interbody spacer according to claim 1, wherein said housing is further configured to have at least one concave portion and at least one convex portion.

3. The interbody spacer according to claim 1, wherein said housing includes a plurality of concave portions.

4. The interbody spacer according to claim 1, wherein said housing includes a plurality of convex portions.

5. The interbody spacer according to claim 1, wherein at least one of the protrusions is configured to be aligned in a different direction to another one of the protrusions.

6. The interbody spacer according to claim 1, wherein said midline portion includes a midline trench opening configured to connect said openings.

7. The interbody spacer according to claim 1, wherein said protrusions are configured to prevent movement of the interbody spacer once the interbody spacer is installed into a vertebrae.

8. The interbody spacer according to claim 1, wherein the interbody spacer is manufactured from a biologically inert material.

9. The interbody spacer of claim 1, wherein said right side includes a bulleted leading edge disposed on an exterior portion of said housing.

10. An interbody spacer assembly, comprising:
an interbody spacer having:
a housing having a top portion, a bottom portion, left and right sides, a midline portion, a front portion, and a back portion, wherein said front and back portions are configured to be disposed between said left and right sides and said midline portion is configured to be disposed between and connecting said front and back portions, wherein said midline, front and back portions and said left and right sides are configured to be disposed between said top and bottom portions to enclose openings on each side of said midline portion;
said front and back portions are configured to include at least one curved portion;
at least one side of said front and back portions includes at least one sidewall trench within said openings;
said midline portion includes a midline trench opening configured to connect said openings; and
said top and bottom portions are configured to include a plurality of protrusions configured to protrude away from said top and bottom portions.

11. The assembly according to claim 10, wherein at least one of said front and back portions is concave and at least another portion is convex.

12. The assembly according to claim 10, wherein the spacer is manufactured from a biologically inert material.

13. The assembly according to claim 10, further comprising a plurality of said interbody spacers.

14. The interbody spacer according to claim 10, wherein said openings and sidewall trench are configured to allow graft and DBM packing during implantation of the interbody spacer into vertebrae.

15. The interbody spacer assembly of claim 10, wherein said right side includes a bulleted leading edge disposed on an exterior portion of said housing.

16. An interbody spacer system, comprising:
an interbody spacer having:
a housing, said housing having a top portion, a bottom portion, a front portion, a back portion, a midline portion, and left and right side portions disposed between said top portion and said bottom portion, said midline portion is configured to be disposed between and connecting said front and back portions forming openings on each side of said midline portion between said top portion and said bottom portion;
at least one of said front or back portions comprising at least one sidewall trench on an interior portion within said openings configured to provide an area for bone graft material during implantation of the interbody spacer between vertebrae; and
a bone graft material positioned within said at least one sidewall trench and said openings.

17. The interbody system of claim 16, wherein said right side includes a bulleted leading edge disposed on an exterior-portion of said housing.

* * * * *